United States Patent [19]

Libin

[11] Patent Number: 5,000,942

[45] Date of Patent: Mar. 19, 1991

[54] ORAL HYGIENE COMPOSITION

[76] Inventor: Barry M. Libin, 15 Thornhedge Rd., Bellport, N.Y. 11713

[21] Appl. No.: 438,803

[22] Filed: Nov. 20, 1989

[51] Int. Cl.⁵ .................. A61K 7/20; A61K 33/40
[52] U.S. Cl. ............................. 424/53; 424/613
[58] Field of Search .............. 429/49, 53, 613, 614, 429/615, 616

[56] References Cited

U.S. PATENT DOCUMENTS

| | | | |
|---|---|---|---|
| 926,280 | 6/1969 | Morrison | 424/49 |
| 947,120 | 1/1910 | Morrison | 424/49 |
| 1,018,240 | 2/1912 | von Furegser | 424/53 |
| 1,536,305 | 5/1925 | Nitardy | 424/49 |
| 1,622,391 | 3/1927 | Nitardy et al. | 424/49 |
| 2,071,043 | 2/1937 | Nitardy | 424/53 |
| 2,436,673 | 2/1948 | Shelton | 424/614 |
| 3,577,521 | 5/1971 | Scheleer et al. | 424/55 |
| 3,995,024 | 11/1976 | Hawking et al. | 424/55 |
| 4,223,003 | 9/1980 | Scheller | 424/53 |
| 4,346,493 | 8/1982 | Goudsmit | 424/49 |
| 4,405,599 | 9/1983 | Smigel | 424/53 |
| 4,603,045 | 7/1986 | Smigel | 424/53 |
| 4,690,776 | 9/1987 | Smigel | 424/53 |
| 4,837,008 | 6/1989 | Rudy et al. | 424/53 |
| 4,891,211 | 1/1990 | Winston | 424/53 |

FOREIGN PATENT DOCUMENTS

| | | | |
|---|---|---|---|
| 2643411 | 4/1977 | Fed. Rep. of Germany . | |
| 2513119 | 3/1983 | France | 424/613 |
| 4244 | of 1907 | United Kingdom | 424/53 |

OTHER PUBLICATIONS

Volnov et al., Chem. Abstr. 66:59340b (1967).
Federov et al., Chem. Abstr. 81:54344f (1974).
Volnov et al., Chem. Abstr. 83:134393c(1975).
Goupil, Chem. Abstr. 87:11477h (1977).
Ito et al, Chem. Abstr. 107:157660r (1987).

*Primary Examiner*—Shep K. Rose
*Attorney, Agent, or Firm*—Michael Ebert

[57] ABSTRACT

An oral hygiene composition in paste or cream form that can be brushed or otherwise applied to the surface of teeth and adjacent gum tissue to create thereon a removable layer that is maintained on these surfaces in an active state for a period of several hours. The composition includes a synergistic blend of magnesium peroxide and calcium peroxide which together release active oxygen at a relatively slow rate. This oxygenation is sustained during the full treatment period to effect a bleaching action removing stains from the teeth surface and serving to whiten and brighten them. The active oxygen also functions as an oxidizing germicidal agent to destroy anerobic bacteria associated with dental plaque and periodontal disease.

11 Claims, No Drawings

ORAL HYGIENE COMPOSITION

BACKGROUND OF INVENTION

1. Field of Invention:

This invention relates generally to preparations for promoting sound oral hygiene, and more particularly to a composition in paste or cream form which when applied as a removable layer onto the surface of teeth and adjacent gum tissue and is maintained thereon for a treatment period of several hours, acts to carry out two functions, the first being cosmetic which is to whiten and brighten the teeth, the second being therapeutic which is to combat dental plaque and the resultant periodontal disease.

2. Status of Prior Art:

In good part, the incidence of dental caries and periodontal disease can be imputed to the formation of plaque on the teeth. It has been reported in the literature that most of the world's population suffers from periodontal disease which is largely responsible for the loss of teeth.

Dental plaque is constituted by a thin layer of mucilaginous film which is subject to invasion by colonizing bacterial Metabolic activity of these bacteria in the presence of dietary carbohydrates leads to the production of acetic and other acids. These acids attack soft gum tissue, thereby causing gingivitis; that is, the reddening and swelling of the normally pink gums, often accompanied by bleeding. These acids also react with the calcium of the teeth and the resultant decalcification of the organic matrix or dentin is such as to allow for the further invasion of bacteria and liquefying enzymes. Hence vital to sound oral hygiene is the reduction and control of dental plaque.

As noted in the Ng et al. U.S. Pat. No. 4,839,156 (1989), it has long been recognized that peroxy compounds such as hydrogen peroxide are effective against dental plaque, gingivitis, periodontitis and traumatic oral lesions. Hydrogen peroxide mouth rinses and other preparations inhibit the colonization and multiplication of the anerobic bacteria associated with dental plaque and periodontal disease. And because hydrogen peroxide functions as a bleaching agent, it will also act to whiten stained or discolored teeth or normal teeth whose hard enamel surface has a somewhat yellowish or grayish tinge.

Most peroxy compounds tend to be unstable in storage, either because they are incompatible with other common ingredients included in the oral hygiene composition, or because they react with these ingredients. As a consequence, the composition loses its capacity to release active or nascent oxygen to attack the anerobic bacteria colonizing the plaque. To overcome this drawback, the Ng et al. patent provides a stable, aqueous, hydrogen peroxide gel.

Also concerned with the stability of hydrogen peroxide is the Winston et al. U.S. Pat. No. 4,812,308 (1989). To create a stable composition, this patent provides a tooth powder which is a mixture of sodium bicarbonate and sodium percarbonate. When this powder mixture makes contact with water, it release active hydrogen peroxide.

Another approach to providing a stable hydrogen peroxide to combat periodontal disease is that taken in the Schaeffer U.S. Pat. No. 4,525,180 (1985) in which a hydrogen peroxide gel is stored in one compartment of a collapsible squeeze tube. Stored in the other compartment is a sodium bicarbonate paste which makes contact with the hydrogen peroxide gel only when the tube is squeezed.

The Clipper et al U.S. Pat. No. 4,537,788 (1985) discloses an oral hygiene preparation in which hydrogen peroxide is combined with other ingredients with which this peroxide is compatible.

The Scheller U.S. Pat. No. 4,223,003 (1980) discloses a dentifrice which may be in paste or powder form and includes magnesium peroxide as an oxidizing agent for removing film from teeth. And the Smigel U.S. Pat. No. 4,405,559 (1982) discloses a dental paste that includes calcium peroxide and sodium perborate as oxidizingagents to remove stain and plaque from the teeth.

The use of hydrogen peroxide as an oxidizing agent to fight plaque and to remove stains present problems, for hydrogen peroxide is not only unstable and can quickly lose efficacy, but it is also not free from toxicity and therefore may have adverse side effects if the dosage is excessive or its use is unduly prolonged. This is also true of other peroxy compounds such as sodium perborate. On the other hand, magnesium peroxide and calcium peroxide are relatively slow oxidizing agents.

SUMMARY OF INVENTION

In view of the foregoing, the main object of this invention is to provide a safe and effective oral hygiene composition in paste or cream form that serves a dual function; the first being cosmetic to whiten and brighten the enamel of the teeth, the second being therapeutic to combat dental plaque which results in periodontal disease.

More particularly, an object of this invention is to provide a composition of the above type that is free of side effects, and which may be safely maintained on the teeth and the adjacent gum tissue for a prolonged period to obtain optimal effects.

Also an object of this invention is to provide an oral hygiene composition which after repeated applications will inhibit the activity of gingival pathogens and their toxic products to a degree imparting a healthier color, form and texture to the treated gingival tissue.

Briefly stated, these objects are attained in an oral hygiene composition in paste or cream form that can be brushed or otherwise applied to the surface of teeth and adjacent gum tissue to create thereon a removable layer that is maintained on these surfaces in an active state for a treatment period of several hours.

The composition includes a synergistic blend of magnesium peroxide and calcium peroxide which together release active oxygen at a relatively slow rate. The oxygenation is sustained during the full treatment period to effect a bleaching action removing stains from the teeth surface and serving to whiten and brighten them. The active oxygen also functions as an oxidizing germicidal agent to destroy anerobic bacteria associated with dental plaque and periodontal disease.

DETAILED DESCRIPTION OF INVENTION

An oral hygiene composition in accordance with the invention for releasing active oxygen is in viscous paste or cream form so that it may be painted, brushed or otherwise applied to the surface of the teeth and to adjacent gingival tissue so as to create a removable layer adherent thereto. This layer is permitted to remain on the surfaces for a treatment period of several hours, say overnight, to cause slow but sustained activity of the oxygen on the enamel of the teeth and on the gum tissue.

The following are the ingredients of this composition whose viscosity may be adjusted in a range extending from a moderately heavy cream to a thick paste.

| | Ingredient | Percentage by Weight |
|---|---|---|
| A. | magnesium peroxide (bleaching, oxidizing and germicidal agent) | from 0.5% to 5% |
| B. | magnesium hydroxide (pH adjuster for the magnesium peroxide in an amount to render the pH non-acidic | from 0.5% to 5% |
| C. | calcium peroxide (bleaching, oxidizing and germicidal agent) | from 0.5% to 5% |
| D. | calcium hydroxide (pH adjuster from the calcium peroxide in an amount to render the pH non-acidic) | from 0.5% to 5% |
| E. | sodium carboxyl methyl cellulose (thickening agent) | from 0.5% to 25% |
| F. | glycerine (gelling agent) | from 3% to 30% |
| G. | de-ionized water (in an amount to confer a suitable wetness to the cream or paste in accordance with its desired viscosity) | from 20% to 60% |
| H. | sorbitol (this acts as a humectant to retain moisture in the composition) | from 10% to 70% |
| I. | magnesium carbonate (cleansing agent) | from 0.5% to 5% |
| J. | magnesium oxide (cleansing agent) | from 0.5% to 5% |
| K. | sodium lauryl sulfate (anionic surfactant having detergent and foaming properties) | from 0.5% to 5% |
| L. | sodium benzoate (preservative) | from 0.5% to 5% |
| M. | methyl paraben (preservative) | from .01% to 1.0% |
| N. | peppermint oil (flavoring agent) | from .01% to 1.0% |
| O. | titanium dioxide (whitening agent) | from .01% to 1.0% |

To avoid any adverse side reaction, it is important that the oxidizing activity of the peroxy agent not take place at a rapid rate as in the case of hydrogen peroxide, but in a slow, sustained fashion over a prolonged treatment period. This is accomplished by blending the magnesium peroxide with the calcium peroxide to provide a peroxy agent which synergistically combines the different oxygen-releasing characteristics of these ingredients.

Magnesium peroxide is virtually insoluble in water. However, when slurried in water, partial hydrolysis takes place with a very slow release of active oxygen. This very slow release allows for a sustained and long lasting effect of oxidation on the enamel surface of the teeth and on the adjacent gingival tissue. Thus when the composition which includes magnesium peroxide is coated on these surfaces and remains thereon for 5 to 8 hours, during this period active oxygen is very slowly released. But the volume of oxygen released per minute is not sufficient to render the composition fully effective for its intended purpose.

Calcium peroxide, on the other hand, is slightly soluble in water and therefore releases active oxygen at a more rapid rate than magnesium peroxide. Hence if used as the sole source of active oxygen, it may be unduly reactive and not completely safe. However, by blending calcium peroxide with the virtually insoluble magnesium peroxide in proper proportions, we have found that one can produce an oxidative reaction at the tooth and gingival tissue surfaces which is relatively rapid but not unduly so, and is therefore efficacious, yet altogether safe.

During the prolonged treatment period in which the composition remains on the surfaces, it acts to slowly burn organic stains that have accumulated on the natural tooth surface or on the surface of a synthetic tooth used by a dentist to replace a missing tooth or on a synthetic tooth section repair a broken tooth. This burning action, which affects stains on the teeth as well as the off-white color of natural enamel, serves to whiten the tooth enamel and therefore has only a cosmetic function.

The whitening of the teeth by this burning activity is enhanced by the whitening agents included in the composition, so that imparted to the tooth surface is a bright, white color.

But whitening and brightening is but one function of the oral hygiene composition, for it also serves therapeutically as an oxidizing germicidal or anti-microbial agent to combat anerobic bacteria lodged in plaque, and in doing so to arrest periodontal disease. Because this treatment is sustained for a prolonged period, at the end of each treatment, there is a perceptible improvement in the condition of the gum tissue. And with repeated treatments, the gum tissue will be restored to its normal healthy, pink, firm condition.

The composition, while it includes to a small degree abrasive constituents, allows for long term brushing of the teeth without inflicting damage to the enamel surfaces.

In preparing the composition, first the glycerine (F), the water (G), the sodium carboxylmethyl cellulose (E) and the sorbitol (H) are intermingled to produce a gel of the desired consistency, after which the other ingredients are stirred into the gel to complete the composition.

It is important to note that the prepared composition is non-acidic or alkaline; that is, it has a pH of 8 or higher. In this state, the composition is inactive and may be stored in a squeeze tube or other suitable sealed container. When, however, the composition is applied orally, it is rendered acidic by the saliva in the mouth, and it then proceeds to release active oxygen.

While there has been disclosed a preferred composition, it is to be understood that changes may be made therein without departing from the invention, as long as the composition includes a blend of magnesium and calcium peroxide. Thus gelling and thickening agents other than those disclosed herein may be used, and other forms of sweeteners and flavoring agents may be employed in the composition.

I claim:

1. An oral hygiene composition in a wet aqueous non-acid or alkaline viscous paste or cream form that can be applied to the surfaces of teeth and their adjacent gingival tissues to create therein a removable layer which is maintained on these surfaces in an active state for a treatment period of several hours, said composition consisting essentially of: from 0.5% to 40% by weight by de-ionixzed water in an amount effective to confer a suitable wetness to the cream or paste containing (a) magnesium peroxide; and (b) calcium peroxide blended with the magnesium peroxide in synergistic proportions resulting in a sustained slow release of active oxygen during said period to effect whitening of the tooth surface and to act as an oxidizing germicidal agent to destroy anerobic bacteria associated with dental plaque coating the surfaces.

2. A composition as set forth in claim 1, further including magnesium hydroxide and calcium hydroxide in an amount adjusting the $P_h$ of the composition so that it is substantially neutral.

3. A composition as set forth in claim 1, further including a thickening agent and a gelling agent in an amount providing the desired form of the composition.

4. A composition as set forth in claim 3, wherein said thickening agent is sodium carboxymethyl cellulose.

5. A composition as set forth in claim 4, wherein said gelling agent is glycerine.

6. A composition as set forth in claim 1, further including sorbitol functioning as a humectant to retain moisture in the composition.

7. A composition as set forth in claim 1, further including sodium lauryl sulfate as a detergent and foaming agent.

8. A composition as set forth in claim 1, further including methyl paraben as a preservative.

9. An oral hygiene method for treating the surfaces of teeth and their adjacent gingival tissue comprising the steps of:
  (a) forming a viscous composition in accordance with claim 1 that consists essentially of a blend of magnesium peroxide and calcium peroxide in synergistic proportions resulting in a sustained slow release of active oxygen;
  (b) applying the composition to the surfaces to form a removable layer thereon; and
  (c) maintaining the layer of the surfaces for a treatment period of several hours sufficient to cause the active oxygen to act as a bleaching agent to whiten the teeth, and to act as a germicidal agent to detroy anerobic bacteria associated with dental plaque.

10. A method as set forth in claim 9, wherein the viscosity of the composition is such as to form a cream or paste that will adhere to the surfaces and remain thereon until the composition is removed.

11. A method as set forth in claim 9, wherein the composition formed is non-acidic to render it inactive, the composition when applied becoming acidic as a result of human saliva to release active oxygen.

* * * * *